United States Patent
Onishi et al.

(10) Patent No.: US 8,376,992 B2
(45) Date of Patent: Feb. 19, 2013

(54) BALLOON CATHETER AND SHEATH FABRICATION METHOD

(75) Inventors: Koji Onishi, Tokyo (JP); Yutaka Yanuma, Tokyo (JP)

(73) Assignee: Olympus Medical Systems Corp. (JP)

( * ) Notice: Subject to any disclaimer, the term of this patent is extended or adjusted under 35 U.S.C. 154(b) by 49 days.

(21) Appl. No.: 12/181,385

(22) Filed: Jul. 29, 2008

(65) Prior Publication Data

US 2010/0030142 A1    Feb. 4, 2010

(51) Int. Cl.
    *A61M 31/00*    (2006.01)
(52) U.S. Cl. .............. 604/103.07; 604/103.1; 606/192
(58) Field of Classification Search ............ 606/194, 606/192; 604/96.01, 101.02, 103, 103.01, 604/103.02, 103.05, 103.06, 103.07, 529, 604/103.08, 103.1, 103.11, 103.12, 544, 604/103.14, 910; 623/1.11
    See application file for complete search history.

(56) References Cited

U.S. PATENT DOCUMENTS

| | | | |
|---|---|---|---|
| 4,188,954 A | | 2/1980 | Patel et al. |
| 5,049,132 A | * | 9/1991 | Shaffer et al. ............ 604/101.02 |
| 5,121,536 A | | 6/1992 | Pike |
| 5,400,789 A | | 3/1995 | Griffith |
| 5,860,963 A | * | 1/1999 | Azam et al. .................. 604/528 |
| 6,231,543 B1 | * | 5/2001 | Hegde et al. ............... 604/96.01 |
| 2002/0010420 A1 | | 1/2002 | Bagaoisan et al. |
| 2004/0199111 A1 | * | 10/2004 | Gershowitz ................... 604/107 |
| 2005/0255317 A1 | * | 11/2005 | Bavaro et al. ................. 428/375 |
| 2007/0055301 A1 | | 3/2007 | Campbell et al. |
| 2008/0200874 A1 | * | 8/2008 | Ferry .......................... 604/103.1 |

FOREIGN PATENT DOCUMENTS

| | | |
|---|---|---|
| JP | 05-220215 | 8/1993 |
| JP | Hei 5-63551 | 8/1993 |
| JP | 10-033681 | 2/1998 |
| JP | 11-244385 | 9/1999 |
| JP | 2001-046378 | 2/2001 |
| WO | WO 00/62852 | 10/2000 |

OTHER PUBLICATIONS

Extended European Search Report dated Dec. 11, 2009 in corresponding European Patent Application No. EP 09 00 9798 (in English language).

* cited by examiner

*Primary Examiner* — Theodore Stigell
(74) *Attorney, Agent, or Firm* — Ostrolenk Faber LLP

(57) ABSTRACT

A balloon catheter including: a flexible sheath which has at least one lumen; and a cylindrical balloon which is fixed to the outer peripheral surface of the sheath and can be inflated with a fluid supplied from the lumen; wherein the sheath has a large diameter portion whose outer diameter is greater than a basic outer diameter thereof, and the balloon is set to have a maximum inner diameter greater than the basic outer diameter when deflated, and is attached to the outer peripheral surface of the large diameter portion.

7 Claims, 9 Drawing Sheets

Prior Art

BALLOON CATHETER AND SHEATH FABRICATION METHOD

BACKGROUND OF THE INVENTION

1. Field of the Invention

The present invention relates to a balloon catheter for use in combination with a side view endoscope in medical treatment and the like, and a method for fabricating a sheath for use in the balloon catheter.

2. Background Art

Conventionally, a balloon catheter with a balloon attached at the distal end has been used as medical equipment for removing gallstones and the like. When removing gallstones with use of this balloon catheter, cannulation is performed from the duodenal papilla into the bile duct, and in the bile duct, the balloon is inflated to about a size which allows the balloon to be contacted with the bile duct wall. Then, the inflated balloon is used to rake gallstones out of the bile duct.

Accordingly, the abovementioned balloon catheter is required to have properties such as a high cannulation capability (insertability) into the bile duct, and a capability of inflating the balloon to a size which allows close contact with the inner wall of the bile duct.

When gallstones are formed in the bile duct, the bile flow is impaired, which often causes expansion of the diameter of the bile duct itself. Therefore, to deal with such a case, there is an increasing demand for a balloon catheter comprising a balloon which is inflatable to a larger diameter.

The maximum inflation diameter of the balloon is mostly determined by the material of the balloon, the dimension of the inner diameter of the balloon when deflated, and the like. Accordingly, to achieve a greater maximum inflation diameter, it is necessary to increase the dimension of the deflated balloon to greater than that of a conventional balloon catheter, if the same material is used for these balloons.

As a balloon catheter which has realized a greater maximum inflation diameter, there is known a balloon catheter in which the inner diameter of the balloon is increased and the catheter's distal end for fixing the balloon is thickened (for example, refer to Japanese Unexamined Utility Model Application, Publication No. Hei. 5-63551).

In addition, as another example, there is also known a balloon catheter comprising a so-called barrel-shaped or lantern-shaped balloon in which only the central portion is formed thick and the axial ends are to be fixed to the catheter are formed thin, so as to increase the maximum inflation diameter of the balloon while retaining thinness of the outer diameter of the catheter's distal end (for example, refer to Japanese Unexamined Patent Application, First Publication No. 2001-46378).

SUMMARY OF THE INVENTION

A first aspect of the present invention is a balloon catheter comprising: a flexible sheath which has at least one lumen; and a cylindrical balloon which is fixed to the outer peripheral surface of the sheath and can be inflated with a fluid supplied from the lumen; wherein the sheath has a large diameter portion whose outer diameter is greater than a basic outer diameter thereof, and the balloon is set to have a maximum inner diameter greater than the basic outer diameter when deflated, and is attached to the outer peripheral surface of the large diameter portion.

The term "basic outer diameter" refers to the outer diameter dimension in a region of the sheath where the large diameter portion is formed.

A second aspect of the present invention is a balloon catheter comprising: a flexible sheath which has at least one lumen; and a cylindrical balloon which is fixed to the outer peripheral surface of the sheath and can be inflated with a fluid supplied from the lumen; wherein the sheath has a small diameter portion on a distal side, and a large diameter portion which is formed to have an outer diameter greater than that of the small diameter portion at equal diameter all over the full length, on a proximal side from the small diameter portion, and the balloon is set to have a maximum inner diameter equal to the large diameter portion when deflated.

A third aspect of the present invention is a method of fabricating a sheath for use in a balloon catheter, comprising: a first step of forming a basic outer diameter portion by softening the distal end of the sheath having an initial outer diameter by heating to a predetermined temperature, and pulling the distal end in the axial direction to make the outer diameter of the distal end smaller than the initial outer diameter; and after the first step, a second step of forming a large diameter portion by reheating a partial region of the basic outer diameter portion excluding the distal end thereof, and making the outer diameter of the partial region greater than the basic outer diameter with aid of residual strain occurring in the basic outer diameter portion.

DETAILED DESCRIPTION OF THE INVENTION

Hereunder is a description of a balloon catheter of a first embodiment of the present invention, with reference to FIG. 1 to FIG. 12.

Figure 1:
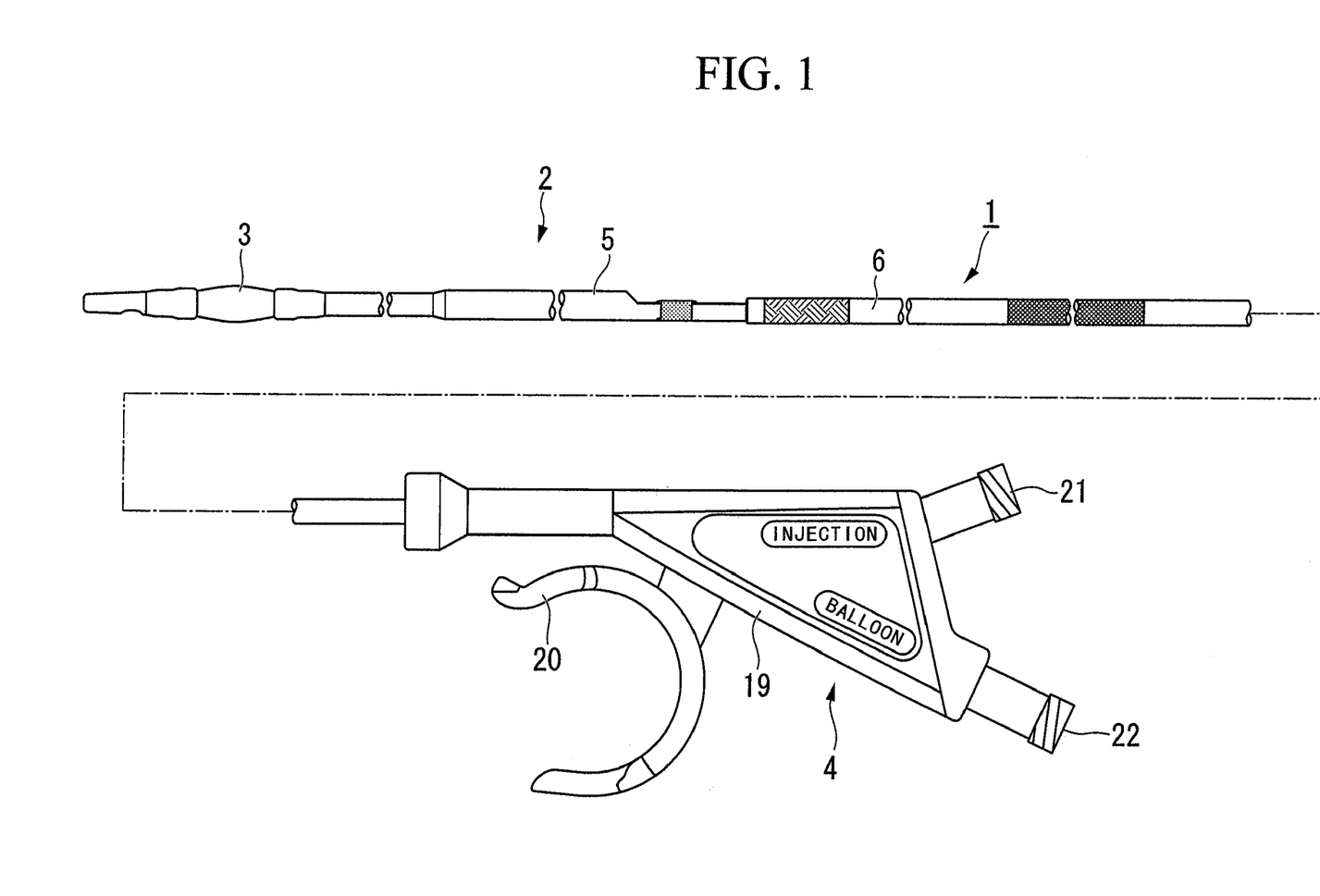
FIG. 1 is an overall view of a balloon catheter of a first embodiment of the present invention.

As shown in FIG. 1, a balloon catheter 1 of the present embodiment comprises; a long and flexible sheath 2, a balloon 3 attached to an outer peripheral surface of the sheath 2, and a controller 4 attached to a proximal end of the sheath 2.

The sheath 2 comprises a first sheath 5 on the distal side, and a second sheath 6 connected to the proximal end of the first sheath 5. As for the materials of the respective sheathes 5 and 6, various types of resins may be suitably employed such as fluorine-based resins including polytetrafluoroethylene (PTFE), polyolefin-based resins, polyurethane, polyamide, and polyamide elastomers.

In the present embodiment, the first sheath 5 to be inserted into the body cavity is formed of a fluorine-based resin in consideration of biocompatibility, insertability into the bile duct (such as firmness, slidability, and flexibility), the slidability with respect to a guide wire, and the like, while the second sheath 6 mostly located in the channel of the endoscope is formed of a rigid and inexpensive resin such as polyamide in consideration of transferability of a pushing force (pushability), tensile strength, production cost, and the like.

The basic outer diameter of the sheath 2 is defined as the outer diameter D1 (refer to FIG. 2) of a region in the sheath 2 where a large diameter portion that will be described later is formed. Its value is set at 1.8 mm, for example.

Figure 2:
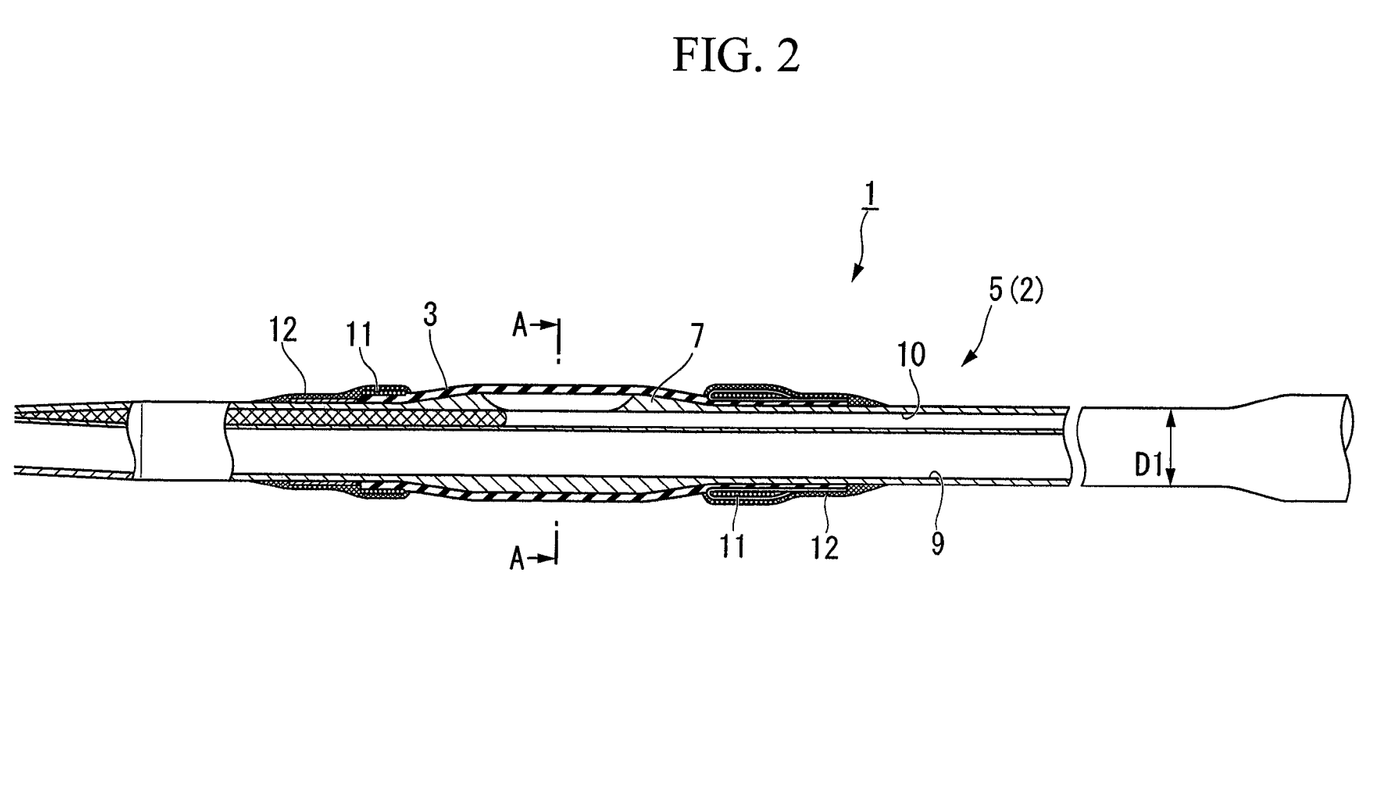
FIG. 2 is an enlarged cross-sectional view in the vicinity of a distal end of the balloon catheter.
Figure 3:
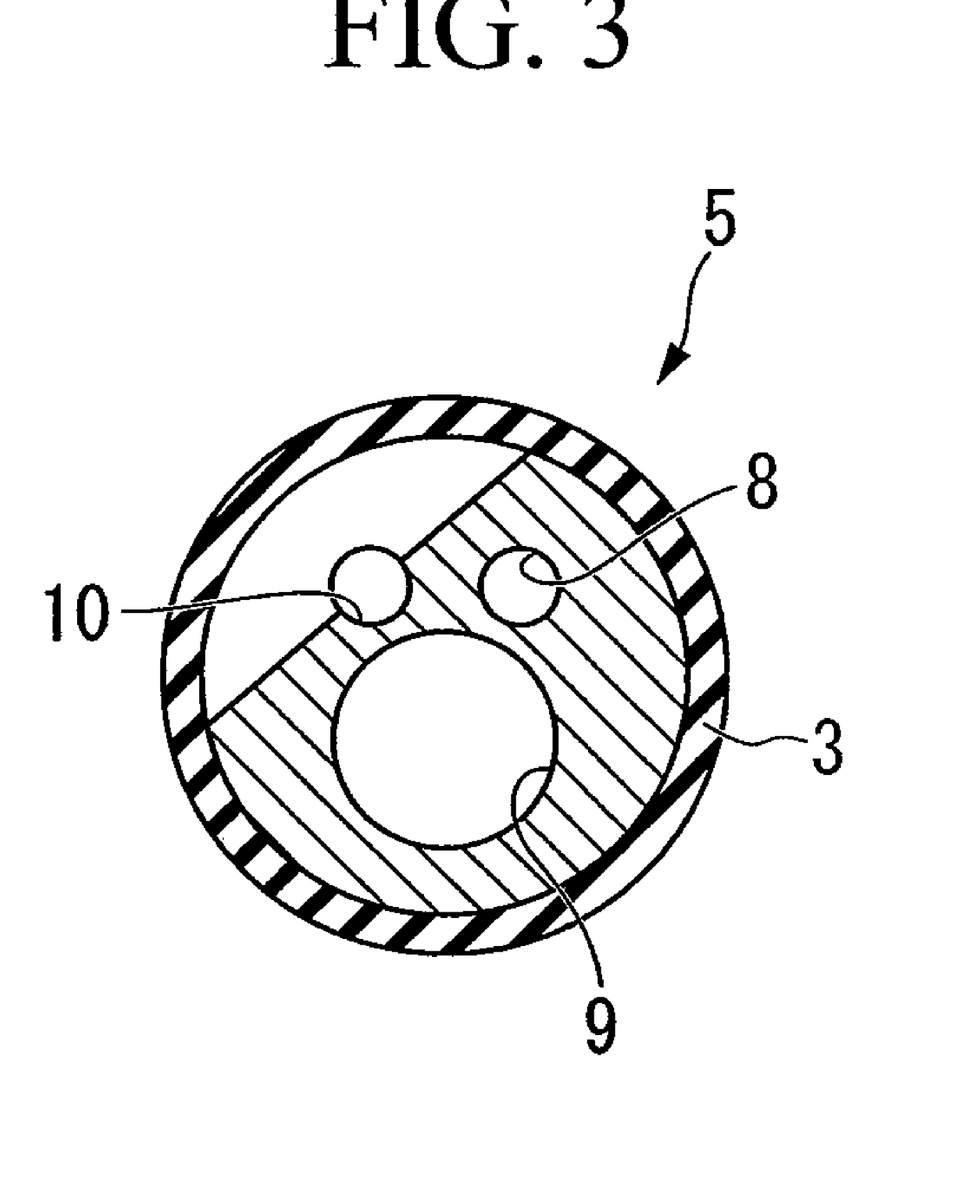
FIG. 3 is a cross-sectional view taken along the line A-A of FIG. 2.

FIG. 2 is an enlarged cross-sectional view of a distal side of the first sheath 5, and FIG. 3 is a cross-sectional view taken along the line A-A of FIG. 2.

As shown in FIG. 2, in a region on a proximal side from the distal end of the first sheath 5 by a predetermined length, for example, about 10 mm, is formed a large diameter portion 7 having an outer diameter greater than the basic outer diameter D1. Axially opposite ends of the large diameter portion are respectively formed in a tapered shape of gradually decreasing diameter. An intermediate portion excluding the opposite ends thereof is set to have a constant diameter at a value greater than the basic outer diameter D1, for example, about 2.4 mm.

As shown in FIG. 3, the first sheath 5 is provided with three lumens: a first lumen 8 for supplying a liquid such as a contrast medium from the distal end; a second lumen 9 for insertion of a guide wire that will be described later; and a third lumen 10 for supplying a fluid into the balloon 3 to effect inflation.

The first lumen 8 communicates from a vicinity of the distal end of the first sheath 5 to the proximal end of the second sheath 6. The second lumen 9 communicates from the distal end of the first sheath 5 which is on the distal side from the large diameter portion 7, to the proximal end of the first sheath 5. The third lumen 10 is open to the outer peripheral surface of the large diameter portion 7, and communicates to the proximal end of the second sheath.

The first sheath 5 takes such a triple lumen structure provided with the respective lumens 8, 9, and 10, while the second sheath 6 takes a double lumen structure provided with the first lumen 8 and the third lumen 10 only. A detailed configuration of a connection between the first sheath 5 and the second sheath 6 will be described later.

The balloon 3 is an approximately cylindrical member formed of an elastic member such as latex rubber, into which the sheath 2 is inserted so as to cover the outer peripheral surface of the large diameter portion 7, and the axially opposite ends of which are fixed to the sheath 2 in an airtight manner.

More specifically, the axially opposite ends of the balloon 3 are fixed to portions which respectively have an outer diameter approximately the same as the basic outer diameter D1, and which are adjacent to the large diameter portion 7, with a thread 11 and an adhesive 12. Instead of such a fixing method using wound thread and an adhesive, other methods such as thermal welding and laser welding may also be appropriately used.

In this way, the axially opposite ends of the balloon 3 are fixed to the sheath 2 in an airtight manner, which thereby enables inflation and deflation of the balloon 3 by supplying and recovering a fluid through the third lumen 10.

The inner diameter of the balloon 3 when deflated is set at about 2.4 mm, which is approximately equal to the outer diameter of the large diameter portion 7. For this reason, in a state where the balloon 3 is attached to the large diameter portion 7, the balloon 3 is closely contacted with the outer peripheral surface of the large diameter portion 7 without the occurrence of sagging.

So as to further reduce the occurrence of sagging, the balloon 3 may also be attached to the large diameter portion 7 in an axially-extended state. In this case, since the effect of the present invention can be achieved as long as the inner diameter of the balloon 3 when deflated is approximately equal to the outer diameter of the large diameter portion 7 after attachment of the balloon, then the inner diameter of the balloon 3 when deflated can be set at about 2.6 mm before attachment of the balloon, which enables a greater inflation diameter.

Figure 4A:
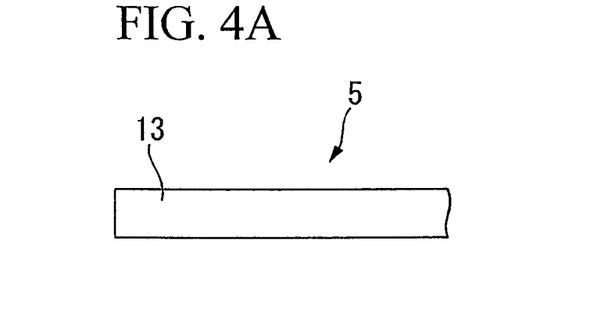
FIG. 4A to FIG. 4C all show a step of forming a large diameter portion on the sheath of the balloon catheter.
Figure 4B:
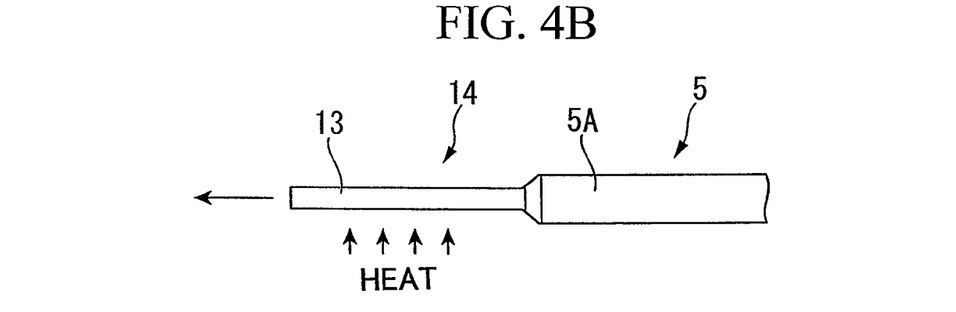
Figure 4C:
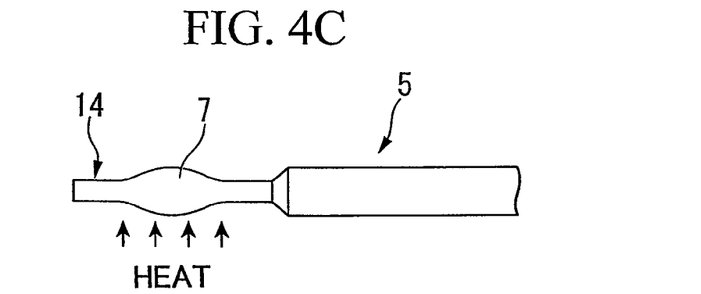
Figure 5:
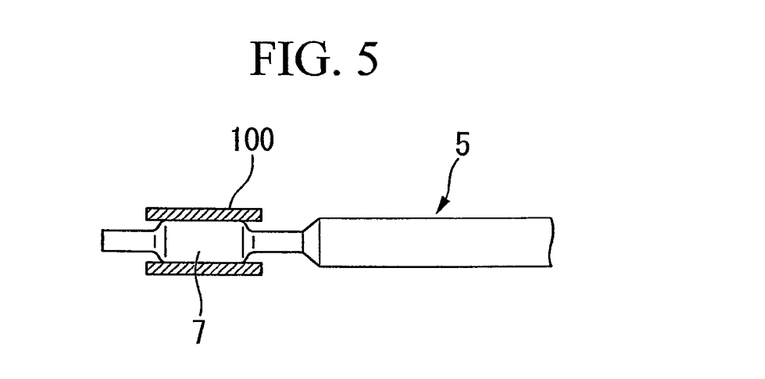
FIG. 5 shows the step of forming the large diameter portion on the sheath.

FIG. 4A to FIG. 5 show an example of the fabrication method for forming the large diameter portion 7 on the first sheath 5.

In this method, firstly as shown in FIG. 4A, the user heats the distal end 13 of the first sheath 5 having an initial outer diameter, until it becomes a softened state. For the heating temperature, the glass transition point of the material of the first sheath 5 may be used as a guide, however the heating temperature may be appropriately adjusted according to various conditions.

Then, when the distal end 13 is sufficiently softened, as shown in FIG. 4B the distal end 13 is pulled in the axial direction to effect elongation, so as to form a basic outer diameter portion 14 having a diameter smaller than the initial outer diameter on the distal side of the first sheath 5 (first step). In this step, the first sheath 5 is formed with the basic outer diameter portion 14 on the distal side and the initial outer diameter portion 5A on the proximal side. In the basic outer diameter portion 14, residual strain occurs due to the elongation.

When the temperature of the basic outer diameter portion 14 once decreases to a degree of losing the plasticity, the user reheats a partial region of the basic outer diameter portion 14 excluding the distal end to about the same degree as that of the first step, so as to soften the region. Then, as shown in FIG. 4C, the softened part of the basic outer diameter portion 14 recedes back in the axial direction due to the residual strain that has occurred in the first step. Accordingly, the outer diameter of the heated part is increased to a value greater than the basic outer diameter (second step). The large diameter portion 7 is formed in this manner.

The formation of the large diameter portion 7 in this manner is easier than a normal shaping method with regard to the formation of the large diameter portion. In particular, when a fluorine-based resin or the like which is difficult to form by a normal shaping method is used, the large diameter portion can be suitably formed by the above fabrication method. In addition, since the initial outer diameter portion 5A which is greater than the basic outer diameter portion 14 remains on the proximal side, the pushability is retained and the operation for pushing the sheath by the user is satisfactorily transferred to the distal end.

The large diameter portion 7 of this embodiment is formed so as to have an approximately constant diameter along the axial direction by performing the abovementioned second step in a state where, as shown in FIG. 5, the sheath 2 is inserted into an approximately cylindrical jig 100.

Figure 6:
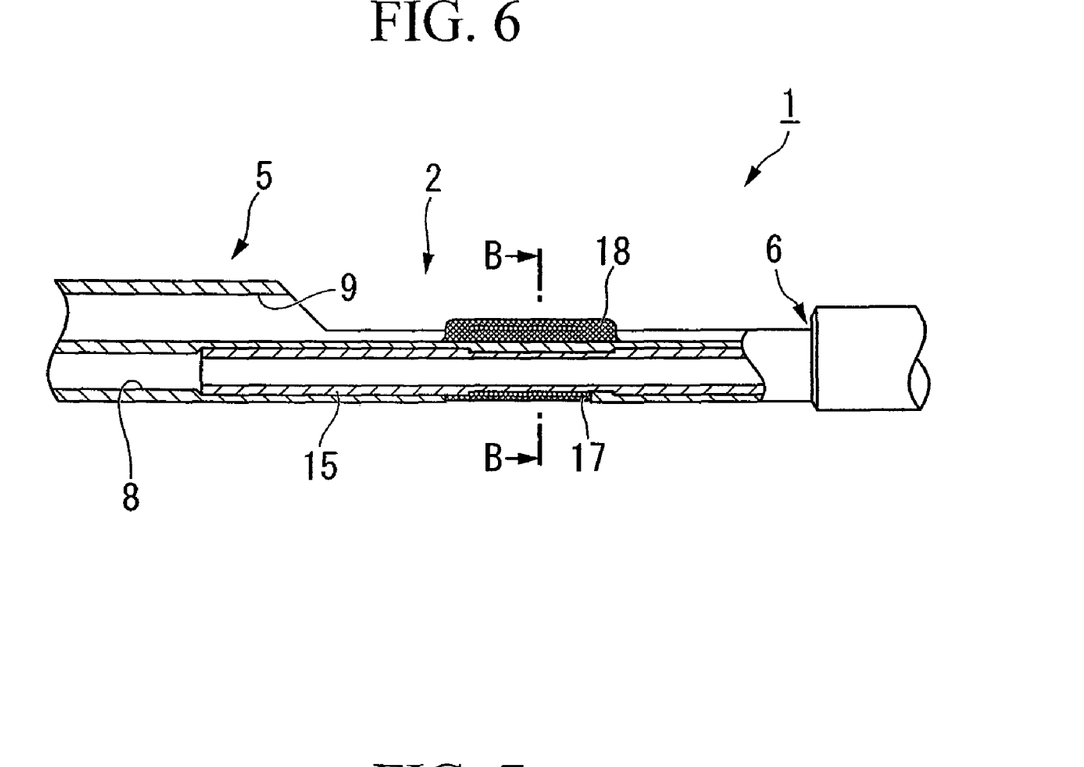
FIG. 6 is an enlarged cross-sectional view of a joint between a first sheath and a second sheath of the sheath.

FIG. 6 is an enlarged cross-sectional view of the joint between the first sheath 5 and the second sheath 6. The second lumen 9 is open in the vicinity of the proximal end of the first sheath 5. That is, the balloon catheter 1 is constituted as a so-called monorail type in which the guide wire is inserted into the first sheath 5 only.

Figure 7:
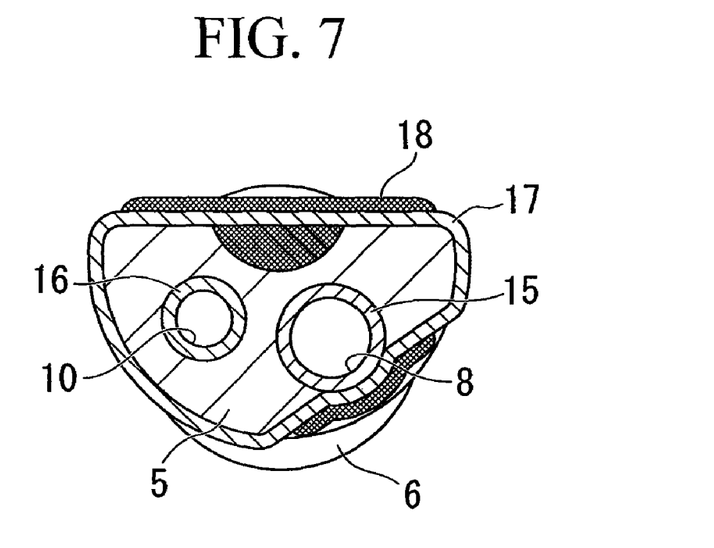
FIG. 7 is a cross-sectional view taken along the line B-B of FIG. 6.

As shown in FIG. 6 and FIG. 7, the first sheath 5 and the second sheath 6 are integrally connected with use of a thread 17 and an adhesive 18 in a state where the first lumens 8 of the respective sheaths are connected with each other by using an auxiliary pipe 15 and the third lumens 10 of the respective sheaths are connected with each other by using an auxiliary pipe 16. The sheath 2 comprising the first sheath 5 and the second sheath 6 is formed in this manner.

Since the approximately cylindrical second sheath 6 takes the double lumen structure comprising the first lumen 8 and the third lumen 10 as mentioned above, there is no need for providing the second lumen 9, and thus for that amount the inner diameters of the first lumen 8 and the third lumen 10 can be set greater. Accordingly, the fluid supplying and recovering efficiency for sending or sucking a gas/liquid etc. through these lumens 8 and 10 can be improved to enable constitution of a balloon catheter which can provide better manipulation performance.

Moreover, it is not necessary to provide the second lumen 9, and thus for that amount the outer diameter of the second sheath 6 can be reduced, which enables combination with a thinner endoscope. In this embodiment, the outer diameter of the second sheath 6 is set at, for example, 2.0 mm so that a general-purpose guide wire having an outer diameter of 0.035 inches (0.089 mm) and an endoscope having a channel's inner diameter of 3.2 mm can be combined therewith for use in a monorail manner.

As shown in FIG. 1 again, the controller 4 attached to the proximal end of the second sheath 6 comprises; a main body 19, a fixation section 20 attached to the main body 19, a first port 21 communicating with the first lumen 8, and a second port 22 communicating with the third lumen 10.

The fixation section 20 is a commonly known type formed in an approximate C-shape, which is capable of fixing the balloon catheter 1 to an endoscope or the like by engaging with the handle or the like of the endoscope as required.

A syringe (not shown) or the like may be connected to the first port 21 so that a contrast medium or the like can be supplied into the first lumen 8.

In the same manner, a syringe (not shown) or the like may be connected to the second port 22, too, so that a fluid such as air or a physiological salt solution for inflating the balloon 3 can be supplied into the third lumen 10.

The operation of the thus constituted balloon catheter 1 during use is described herein with reference to an example of manipulation for removing gallstones.

Figure 8:
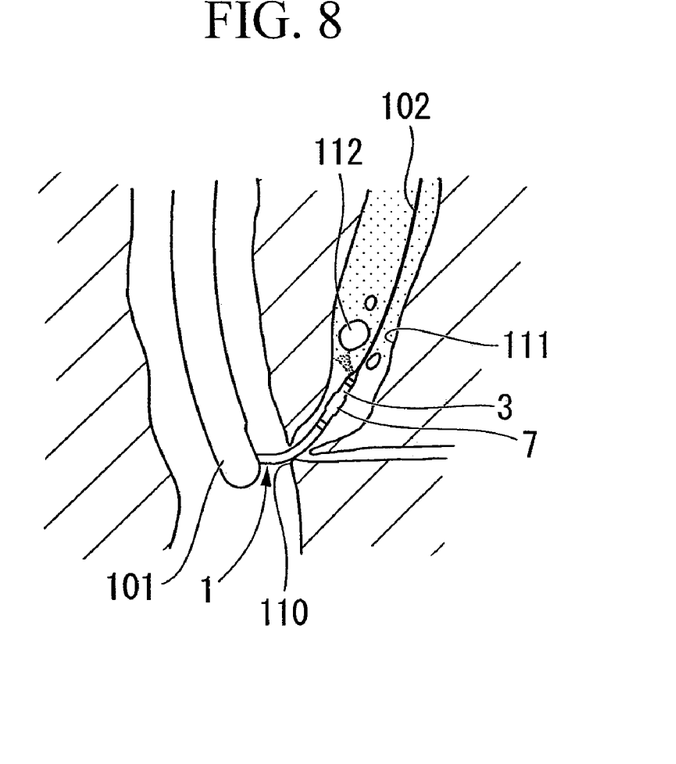
FIG. 8 shows the operation of the balloon catheter during use.

Firstly, the user inserts a side view endoscope from a natural opening such as the mouth into the body cavity of the patient, and moves the distal end of the endoscope 101 forward to a vicinity of the duodenal papilla 110 as shown in FIG. 8.

Next, the user inserts the guide wire 102 from the forceps port (not shown) of the endoscope 101 and makes the distal end of the guide wire 102 protrude toward the duodenal papilla 110 while appropriately operating a raising base (not shown). Then, the distal end of the guide wire 102 is inserted from the duodenal papilla 110 into the bile duct 111.

Next, the user inserts the proximal end of the guide wire 102 into the distal opening of the second lumen 9 of the balloon catheter 1 and makes it protrude from the proximal opening, to thereby insert the guide wire 102 into the second lumen 9. Then, the balloon catheter 1 is inserted from the forceps port into the channel of the endoscope 101, and is moved along the guide wire 102 into the bile duct 111.

At this time, the deflated balloon 3 is closely contacted with the large diameter portion 7 without sagging, and thus will not be torn by being caught on the raising base or the like.

After the balloon catheter 1 has been inserted into the bile duct 111, the user operates a syringe (not shown) connected to the first port 21 to eject a contrast medium from the distal end of the first lumen 8, and confirms the location of the gallstones 112 under radioscopy. Then, the balloon catheter is moved forward deeply into the bile duct 111 until the large diameter portion 7 is located at the rear of the gallstones 112.

At this time, if the large diameter portion 7 is made radiopaque by mixing a radiopaque material in the material for forming the sheath 2, in particular the large diameter portion 7, then the positional relation between the gallstones 112 and the large diameter portion 7 can be readily and accurately comprehended by the user.

Figure 9:
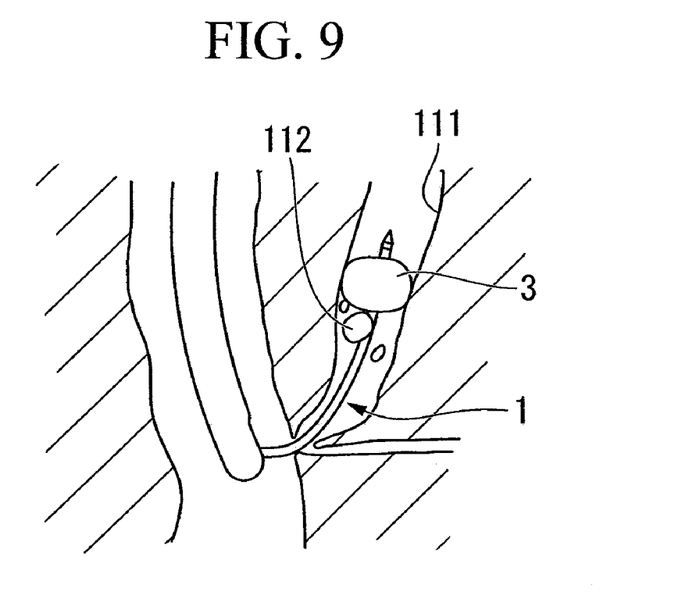
FIG. 9 shows the operation of the balloon catheter during use.

When the large diameter portion 7 has been moved forward to reach the rear of the gallstones 112, the user operates a syringe (not shown) connected to the second port 22 to supply air or a fluid such as a physiological salt solution into the third lumen 10. The supplied fluid is then injected into the cavity of the balloon 3 from the opening of the third lumen 10 provided on the outer peripheral surface of the large diameter portion 7, and as a result the balloon 3 is inflated as shown in FIG. 9.

The maximum inner diameter of the balloon 3 when deflated is set at about 2.4 mm, which is greater than that of a general balloon for use in stone removal. Accordingly, even if the inner diameter of the bile duct 111 is expanded up to about, for example, 20 mm due to bile stasis or the like because of the gallstones 112, the balloon 3 can be inflated to have a diameter approximately the same as that of the bile duct 112 to effect close contact with the inner wall of the bile duct 111.

The user then moves the balloon catheter 1 back toward the duodenal papilla 110 while keeping the balloon 3 inflated. Along with this operation, the gallstones 112 are moved toward the duodenal papilla 110 by being raked by the balloon 3.

Figure 10:
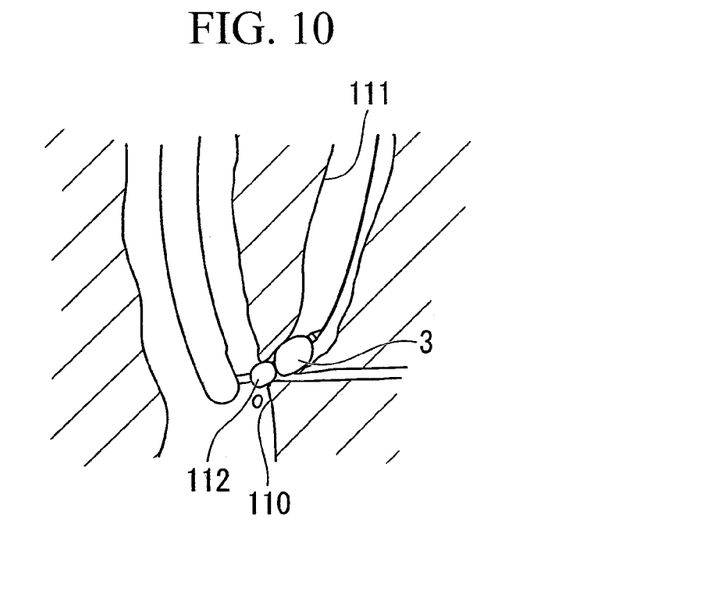
FIG. 10 shows the operation of the balloon catheter during use.

As shown in FIG. 10, when the user withdraws the balloon catheter 1 from the bile duct 111 through the duodenal papilla 110 while appropriately narrowing the balloon 3, the gallstones 112 are removed from the bile duct 111 to thereby complete the manipulation.

In the balloon catheter described in the abovementioned Japanese Unexamined Utility Model Application, Publication No. Hei. 5-63551, the distal end is thickened and hardened to thereby impair the cannulation capability into the duodenal papilla. Therefore, the manipulation becomes complicated, which leads to a problem of increases in the manipulation time and associated invasion into the patient.

Figure 16:
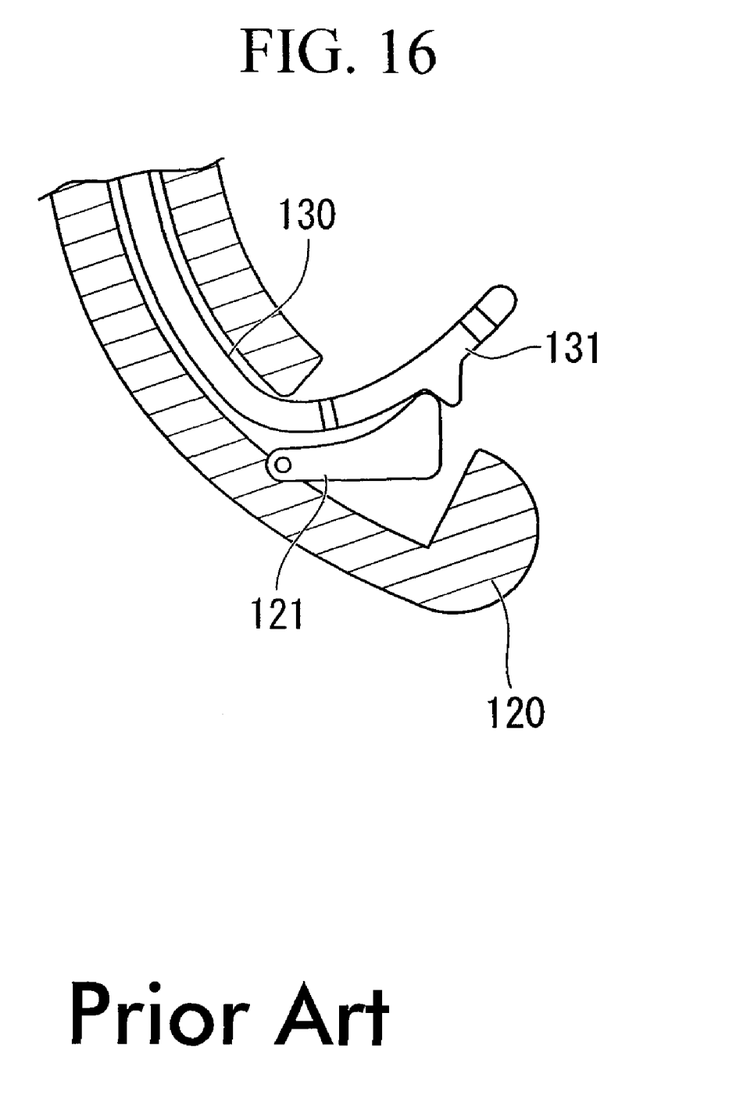
FIG. 16 shows a distal end of a conventional balloon catheter with a balloon having a large inflation diameter attached thereto.

In addition, in the balloon catheter described in Japanese Unexamined Patent Application, First Publication No. 2001-46378, the central portion of the balloon is not closely contacted with the outer surface of the catheter, which causes the occurrence of sagging. Therefore, there has been a problem in that: as shown in FIG. 16, when the balloon 131 of the catheter 130 passes by the side of the raising base 121 of the side view endoscope 120, the balloon is torn because the sagged portion is caught on the projection of the raising base 121 or the like.

According to the balloon catheter 1 of this embodiment, since the sheath 2 is provided with the large diameter portion 7 having an outer diameter greater than the basic outer diameter D1 and the balloon 3 is attached to the outer peripheral surface of the large diameter portion 7, then even a balloon whose diameter when deflated is set large so as to obtain a greater inflation diameter can be attached to the sheath without the occurrence of sagging.

Accordingly, when the balloon catheter is inserted into the forceps port of the endoscope, protruded from the distal end of the channel disposed with the raising base, or withdrawn into the channel, the balloon can be suitably prevented from being caught thereon and torn.

In addition, since the axially opposite ends of the large diameter portion 7 are respectively formed in a tapered shape of gradually decreasing diameter, then the insertability of the sheath can be satisfactorily configured even with the large diameter portion 7.

Furthermore, the axially opposite ends of the balloon 3 are fixed to portions of the outer surface of the sheath which respectively have an outer diameter smaller than that of the large diameter portion 7, and which are adjacent to the large diameter portion 7. Accordingly, since the step made by the large diameter portion 7 functions as a stopper against the fixation section, it is possible to suitably prevent the axial displacement of the balloon 3 occurring when the balloon catheter 1 is being inserted or when the gallstones are being raked by the balloon.

In this embodiment, the description was made with reference to an example where the large diameter portion 7 excluding the tapered opposite ends is formed to have an approximately constant outer diameter. However, instead of this, as a modified example shown in FIG. 11, a large diameter portion 7A may also be formed in an approximately spindle shape which has the greatest outer diameter in the axial center. In this case, since the surface of the sheath 2 can be smoothly formed as a whole, the insertability of the balloon catheter 1 and the withdrawal property at the time of stone removal can be further improved.

Figure 11:
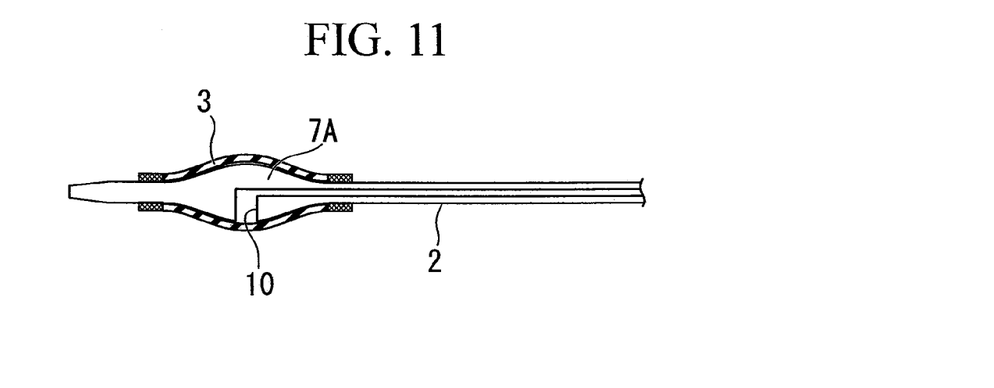
FIG. 11 is a cross-sectional view showing a distal end of a modified example of the balloon catheter of the same embodiment.

Such a large diameter portion 7A can be readily formed by not using the cylindrical jig 100 in the abovementioned second step. When the large diameter portion is to be formed in such a shape, it is preferable to form the balloon in a so-called barrel-shape or lantern-shape fitting the large diameter portion because the occurrence of sagging is more suitably prevented.

Figure 12:
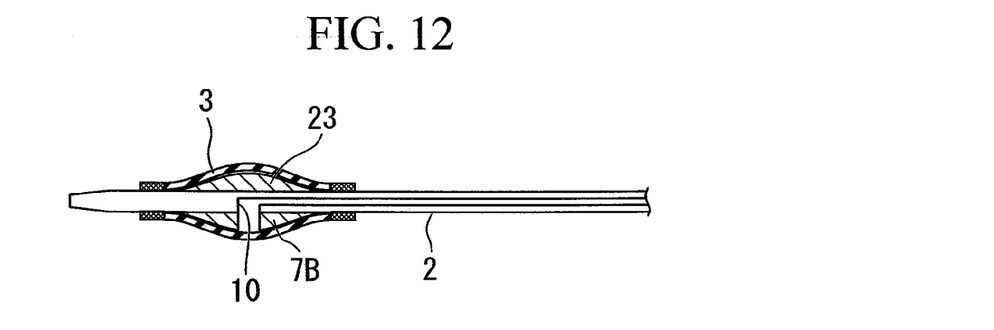
FIG. 12 is a cross-sectional view showing a distal end of another modified example of the balloon catheter of the same embodiment.

In addition, as a modified example shown in FIG. 12, a large diameter portion 7B may also be formed by attaching a spacer 23, which is formed in a desired shape, to the outer peripheral surface of the approximately cylindrical sheath 2. By so doing, a desired shape of the large diameter portion can be readily provided on the sheath by using an easy-to-shape material.

Moreover, if such a spacer is used, there is no need for generating residual strain in the basic outer diameter portion, and therefore the first sheath may also be formed by joining the basic outer diameter portion and the initial outer diameter portion which have been separately formed.

Furthermore, if the spacer 23 is formed of a soft material, damage of the balloon when touching the projection of the raising base can be reduced. In addition, since hardening of the sheath 2 associated with the provision of the large diameter portion can be minimized, the sheath 2 can readily follow the passage of the curved bile duct and the like, which provides a high insertability into the bile duct and the like.

Furthermore, in this embodiment, the description was made with reference to an example where the first sheath 5 and the second sheath 6 are formed of different materials. However they may also be formed of the same material.

Figure 13:
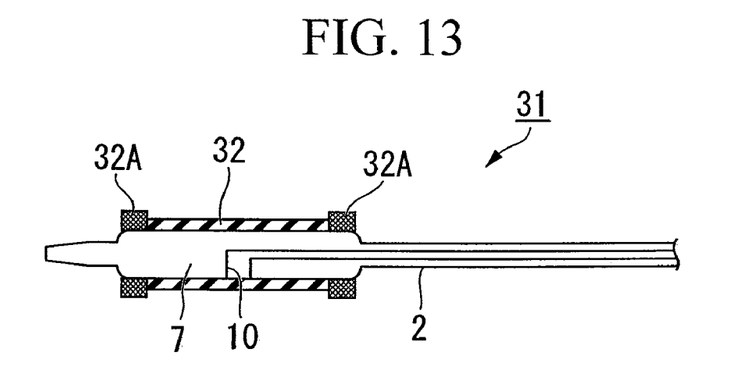
FIG. 13 is a cross-sectional view showing a distal end of a balloon catheter of a second embodiment the present invention.
Figure 14:
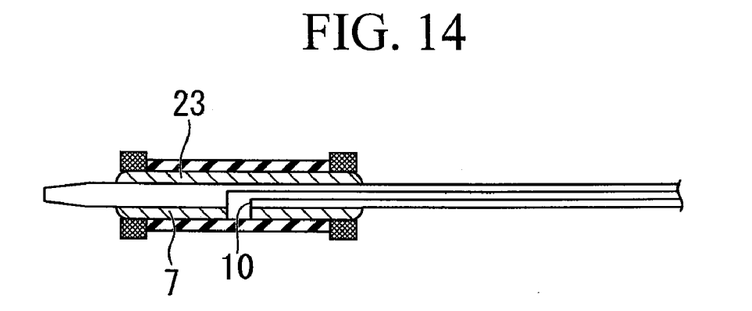
FIG. 14 is a cross-sectional view showing a distal end of a modified example of the balloon catheter of the same embodiment.

Next is a description of a second embodiment of the present invention, with reference to FIG. 13 and FIG. 14. The difference between the balloon catheter of this embodiment and the abovementioned balloon catheter 1 of the first embodiment is the position at which the balloon is fixed to the sheath.

The same reference symbols are used for components in common with the abovementioned first embodiment, and overlapping description is omitted.

FIG. 13 is a cross-sectional view showing a distal end of a balloon catheter 31 of the present embodiment. Similar to the first embodiment, the sheath 2 is provided with three lumens. However, for the sake of easy understanding of the structure, only the third lumen 10 is shown herein.

The shape of the large diameter portion 7 is approximately the same as that of the first embodiment, and is formed to have an approximately constant outer diameter along the axial direction. The balloon 32 is formed in an approximately cylindrical shape to have an outer diameter, when deflated, approximately the same as the large diameter portion 7 along the axial direction. The axially opposite ends 32A of the balloon 32 are fixed to the sheath 2 in an airtight manner, by attaching them to the outer peripheral surface of the large diameter portion 7 with use of a thread, an adhesive, and the like.

The balloon catheter 31 of this embodiment is also able to provide the same effect to that of the balloon catheter 1 of the first embodiment.

Moreover, since the axially opposite ends 32A of the balloon 32 are fixed to the outer peripheral surface of the large diameter portion 7 whose outer diameter is approximately constant along the axial direction, then wrinkles, sagging, and the like hardly occur in the fixed ends 32A even if the cylindrical balloon 32 were used. Accordingly, there is no need of modification to reduce the inner diameter of the axial ends of the balloon so as to eliminate sagging and the like in the fixed part. Therefore, the balloon modification can be omitted so that the balloon catheter can achieve better production efficiency.

In this embodiment, as shown in the modified example of FIG. 14, the large diameter portion 7 may also be formed with use of a spacer 23. In this case, since the outer diameter of the large diameter portion is approximately constant along the axial direction, there is no need of shaping the spacer 23 in a special manner except for providing a hole that communicates with the third lumen 10, and it is possible to improve the production efficiency as compared with the modified example of FIG. 12 where the spacer 23 is used in a similar way.

Figure 15:
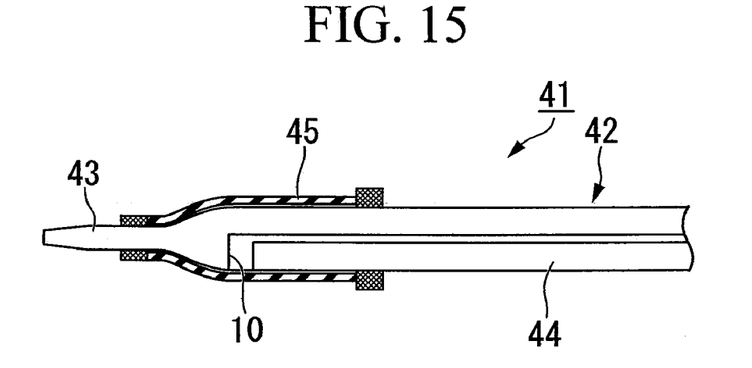
FIG. 15 is a cross-sectional view showing a distal end of a balloon catheter of a third embodiment the present invention.

Next is a description of a third embodiment of the present invention, with reference to FIG. 15. The difference between the balloon catheter of this embodiment and the abovementioned balloon catheter 1 of the first embodiment is the shape of the sheath.

The same reference symbols are used for components in common with the respective abovementioned embodiments, and overlapping description is omitted.

FIG. 15 shows a distal end of a balloon catheter 41 of this embodiment. Regarding the lumen, FIG. 15 shows only the third lumen 10 similar to FIG. 13.

The sheath 42 of the balloon catheter 41 comprises only a small diameter portion 43 on the distal side and a large diameter portion 44 on the proximal side from the small diameter portion 43. The large diameter portion 44 is continuous at an approximately constant diameter up to the proximal end of the sheath 42. The outer diameter of the large diameter portion 44 is set at about 2.4 mm, which is approximately the same as that of the large diameter portion of the other embodiments.

The distal end of the balloon 45 is fixed to a part of the small diameter portion 43 which is adjacent to the large diameter portion 44. The proximal end thereof is fixed to the outer peripheral surface of the large diameter portion 44.

With the balloon catheter 31 of this embodiment, similar to the balloon catheter 1 of the first embodiment, the balloon can be prevented from being torn due to catching on the raising base or the like of the endoscope.

In addition, since the large diameter portion 44 is continuous at an approximately constant diameter up to the proximal end of the sheath 42, the structure is simplified. As a result, there is no need of a step such as the abovementioned second step in the production, so that the production cost can be reduced.

As mentioned above, while preferred embodiments of the present invention have been described, it should be understood that these are exemplary of the invention and are not to be considered as limiting. Various modifications can be made without departing from the spirit or scope of the present invention.

For example, in the respective embodiments mentioned above, the description was made with reference to an example where the balloon catheter is for use in stone removal to extract gallstones or the like. However, the balloon catheter of the present invention is not limited to this, and may also be used, for example, as a balloon catheter for use in expansion of narrowed luminal organs.

Moreover, in the respective embodiments mentioned above, the description was made with reference to an example where the sheath has three lumens of first through third lumens. However, instead of this, for example, if the first and second lumens become unnecessary because of such a change in usage as mentioned above, the balloon catheter of the present invention may also be constituted by appropriately omitting these lumens.

Furthermore, the friction coefficient of the outer peripheral surface of the large diameter portion may be set higher than that of the outer peripheral surface of other parts of the sheath by forming minute corrugations on the outer peripheral surface of the large diameter portion by means of plasma treatment or the like. By so doing, the friction between the attached balloon and the large diameter portion is increased, which thereby enables prevention of the occurrence of wrinkles and sagging caused by the balloon sliding on the outer surface of the large diameter portion.

In addition, the present invention is not to be considered as being limited by the forgoing description, and is only limited by the scope of the appended claims.

What is claimed is:

1. A balloon catheter comprising:
a flexible sheath which has at least one lumen; and
a cylindrical balloon which is fixed to an outer peripheral surface of said sheath and can be inflated with a fluid supplied from said lumen; wherein
said sheath includes a portion having a basic outer diameter and a large diameter portion whose outer diameter is greater than the basic outer diameter,
the large diameter portion having a sheath wall thickness which is greater than a sheath wall thickness of the portion having the basic outer diameter,
the large diameter portion is provided with a supply hole supplying the fluid to the cylindrical balloon,
the supply hole communicates with a cavity of the cylindrical balloon,
the portion having the basic outer diameter is disposed at both ends of the large diameter portion, such that the large diameter portion is located directly between portions having the basic outer diameter;
said balloon is set to have a maximum inner diameter greater than said basic outer diameter when deflated, and a longitudinal position of the maximum inner diameter corresponds to a position of the large diameter portion, and
said balloon is attached at axially opposite ends of the balloon to said sheath at the location of the basic outer diameter so as to cover the outer peripheral surface of said large diameter portion when said balloon is deflated.

2. The balloon catheter according to claim 1, wherein the outer diameter of said large diameter portion is set at a value the same as, or greater than, said maximum inner diameter of said balloon.

3. The balloon catheter according to claim 1, wherein
said balloon is formed in a spindle shape which has a maximum inner diameter in an axial center, and
said large diameter portion is formed in a spindle shape which fits said balloon to effect close contact with said balloon when the balloon is deflated.

4. The balloon catheter according to claim 1, wherein said large diameter portion is formed by a spacer which is made of a material softer than that of said sheath, and which is attached to the outer peripheral surface of said sheath.

5. The balloon catheter according to claim 1, wherein said large diameter portion is formed by a radiopaque spacer which is attached to the outer peripheral surface of said sheath.

6. The balloon catheter according to claim 1, wherein
said large diameter portion is formed integrally with said sheath using the same material, and
said sheath is radiopaque.

7. The balloon catheter according to claim 1, wherein a friction coefficient of the outer peripheral surface of at least a part of said large diameter portion to which said balloon is attached is higher than that of the outer peripheral surface of other parts of the sheath.

* * * * *